United States Patent

Fornasari et al.

Patent Number: 5,321,188
Date of Patent: Jun. 14, 1994

[54] PROCESS AND CATALYST FOR CONVERTING METHANE INTO HIGHER HYDROCARBON PRODUCTS

[75] Inventors: Giuseppe Fornasari, Cremona; Stefano Palmery; Giampiero Piro, both of Milan; Giuseppe Bellussi, Piacenza, all of Italy

[73] Assignees: Eniricerche S.p.A.; Snamprogetti S.p.A., both of Milan, Italy

[21] Appl. No.: 22,660

[22] Filed: Mar. 1, 1993

Related U.S. Application Data

[63] Continuation of Ser. No. 810,695, Dec. 19, 1991, abandoned.

[30] Foreign Application Priority Data

Dec. 21, 1990 [IT] Italy .................. 22483 A/90

[51] Int. Cl.$^5$ ................................ C07C 2/00
[52] U.S. Cl. ........................ 585/500; 585/700; 585/520; 585/530; 585/654; 585/656; 585/658; 585/943
[58] Field of Search ............ 585/500, 700, 520, 530, 585/654, 656, 658, 943

[56] References Cited

U.S. PATENT DOCUMENTS 4,814,538  3/1989  Devries et al. ............ 585/500
4,996,382  2/1991  Matsuura et al. .......... 585/500

Primary Examiner—Patrick P. Garvin
Assistant Examiner—E. D. Irzinski
Attorney, Agent, or Firm—Shea & Gould

[57] ABSTRACT

Methane is converted into higher hydrocarbon products, and especially into ethane and ethylene, by oxidative coupling, by bringing a gaseous mixture containing methane and oxygen into contact at high temperature for a short contact time with a solid catalyst formed from lithium oxide, an alkaline earth metal oxide (preferably of magnesium) and a lanthanide oxide (preferably of neodymium or lanthanum), in which the lithium content is less than 0.20% by weight and the atomic ratio of the alkaline earth metal to the lanthanide varies from 0.8/1 to 8/1, said catalyst being obtained by:
  preparing a mixture of lithium, alkaline earth metal and lanthanide oxides in which the lithium content exceeds 1% by weight; and
  reducing the lithium content of the mixture to less than 0.20% by weight by high temperature thermal treatment conducted at least partly in an oxidizing atmosphere.

11 Claims, 1 Drawing Sheet

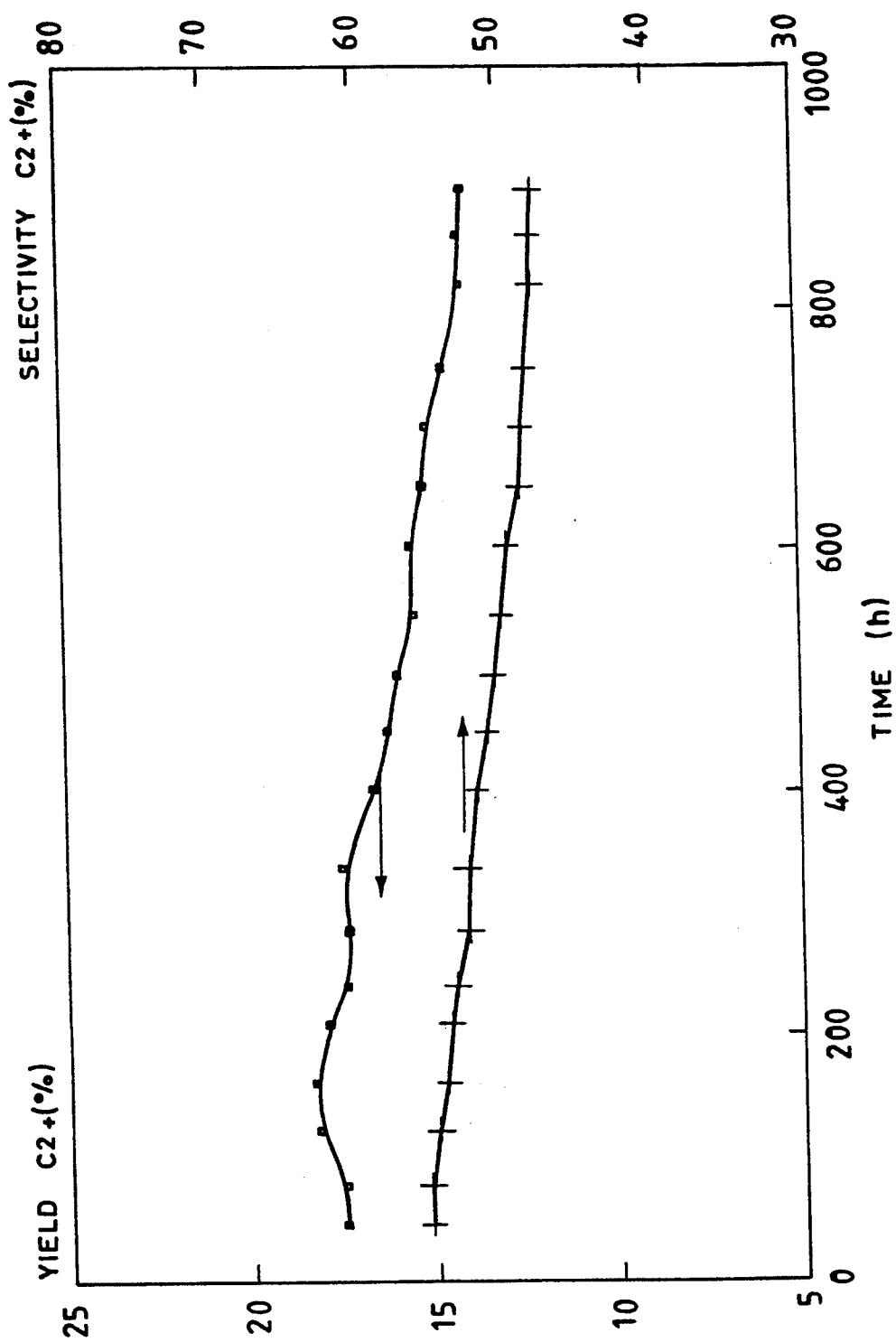

PROCESS AND CATALYST FOR CONVERTING METHANE INTO HIGHER HYDROCARBON PRODUCTS

This is a continuation of application Ser. No. 07/810,695 filed Dec. 19, 1991 now abandoned.

This invention relates to the conversion (oxidative coupling) of methane into higher hydrocarbons and a long-life active selective catalyst for this conversion.

Processes and catalysts are under development for converting methane into higher hydrocarbon products useful as chemicals, as energy vectors or as products useful in reducing the drawbacks of transporting methane from remote areas.

Of the proposed processes, particular attention has been given to oxidative coupling by which methane is converted, in the presence of an oxidizing agent at high temperature over suitable catalysts, into higher hydrocarbons, and especially ethane and ethylene. The oxidizing agent usually used for this purpose is oxygen or air. Catalysts which demonstrate activity in methane oxidative coupling processes are generally formed from metal oxides, the technical and patent literature describing catalysts containing an alkaline metal oxide and an alkaline earth metal oxide, plus possibly one or more transition metal or rare earth oxides. For this known art reference should be made in particular to the description of Z. K. Biyngli et al. in Applied Catalysis 39 (1988), pp 185-190, to European patent application publication No. 196,541 and to U.S. Pat. No. 4,728,636.

Catalysts containing an alkaline metal oxide, and particularly lithium oxide, demonstrate high initial activity in methane oxidative coupling processes, but unfortunately this activity falls off rapidly with time, the fall-off being accompanied by loss of lithium from the catalyst. It has been found experimentally that this lithium loss proceeds until the residual lithium content is of the order of 0.1% by weight, this being independent, within wide limits, of the lithium concentration in the initial catalyst.

According to the present invention, it has now been found possible to prevent or at least reduce the deactivation phenomenon accompanying the lithium loss in certain methane oxidative coupling catalysts, by particular expedients adopted during the catalyst preparation. These expedients are essentially based on the unexpected observation that the residual activity of a catalyst impoverished in lithium depends on the initial lithium concentration and the manner of its elimination.

In accordance therewith the present invention provides a process for converting methane (by oxidative coupling) into higher hydrocarbon products over a metal oxide catalyst, said process being characterised in that a gaseous mixture containing methane and oxygen is brought into contact, at a temperature of at least 650° C., with a solid catalyst formed from lithium oxide, an alkaline earth metal oxide and a lanthanide oxide, in which the lithium content is less than 0.20% by weight and the atomic ratio of the alkaline earth metal to the lanthanide varies from 0.8/1 to 8/1, said catalyst being obtained by:

preparing a mixture of lithium, alkaline earth metal and lanthanide oxides in which the lithium content exceeds 1% by weight; and reducing the lithium content of the mixture to less than 0.20% by weight by high temperature thermal treatment conducted at least partly in an oxidizing atmosphere.

In the preferred embodiment, the lithium content of the initial oxide mixture varies from 4 to 10% by weight, the lithium content being reduced to a value of the order of 0.1% by weight in the final catalyst. In addition, in the preferred embodiment the atomic ratio of the alkaline earth metal to the lanthanide in the oxide mixture and in the final catalyst varies from 2/1 to 4/1. The alkaline earth metal is preferably magnesium and the lanthanide is preferably neodymium or lanthanum.

The metal oxide mixture of high lithium content, constituting the catalyst precursor of the present invention, can be obtained from water-soluble compounds of lithium, of the alkaline earth metal and of the lanthanide, operating with the sol-gel method or impregnation method.

If the sol-gel method is used, the procedure is as follows:

an aqueous and/or alcoholic solution of a soluble compound of a lanthanide and of the alkaline earth metal is prepared, an aqueous and/or alcoholic solution of the lithium compound and an organic base is prepared, the two solutions are mixed together to form a gel, and the gel obtained is dried.

If the impregnation method is used the procedure comprises preparing a precipitate of the lanthanide and alkaline earth metal oxides and impregnating these oxides with the lithium compound. Lanthanide compounds which can be employed for this purpose are the organic acid salts such as acetates, the inorganic acid salts such as nitrates, and the organo-metallic derivatives such as alkoxides. Alkaline earth metal compounds suitable for this purpose are conveniently chosen from the aliphatic organic acid salts, especially the acetates. The lithium compounds can be chosen from lithium hydroxide and carbonate.

Operating as stated heretofore, a metal oxide mixture is obtained, a critical aspect being that the lithium content of this mixture must exceed 1% by weight, and is preferably between 4 and 10% by weight. According to the present invention the catalyst precursor obtained in this manner is subjected to high temperature thermal treatment conducted at least partly in an oxidizing atmosphere, to reduce the lithium content to below 0.20% by weight and preferably to a value of the order of 0.1% by weight. For this purpose the catalyst precursor can be heated in an oxygen stream or an oxygen-containing stream, such as air, to a temperature generally variable between 700° and 900° C., for a time suitable for reducing the lithium content to the desired value. The suitable time for this purpose can vary generally from 3 to 30 hours.

According to one embodiment, the lithium is partly eliminated from the precursor under the aforestated oxidizing conditions and is then reduced to the desired value in the presence of methane and oxygen, operating at a temperature of the order of 700°-800° C. The methane oxidative coupling reaction is effected by operating with the catalyst, prepared as heretofore described, in the form of a fixed bed to which a gaseous stream is fed containing methane and oxygen possibly diluted with an inert gas, with a methane/oxygen molar ratio of between 1.5/1 and 10/1 and preferably between 1.8/1 and 5/1. The oxygen can be fed in pure form or as air or oxygen-enriched air. The procedure can be carried out under pressure but is preferably carried out without overpressure, at a temperature generally variable between 650° and 1000° C. and preferably of the order of 800°–950° C. with a short contact time generally of the order of 0.0005–0.02 minutes per gram of catalyst per millilitre of gas feed.

When operating according to the present invention, high methane conversion and high selectivity of the methane converted into higher hydrocarbons are obtained, with the catalyst activity and selectivity remaining unaltered for an unexpectedly long time period.

The following experimental examples are given to better illustrate the present invention. From these examples it will be noted that optimum performance is obtained only for a certain range of initial lithium concentration in the catalyst precursor. Precursors with a low initial lithium content are poorly selective towards the desired reaction.

EXAMPLE 1

14.3 g of $Mg(CH_3COO)_2.4H_2O$ are dissolved in a beaker containing 15 g of $H_2O$ acidified with 0.5 ml of $HNO_3$ (65% by weight). After acidifying with a further 1.5 ml of $HNO_3$ (65% by weight), 10.9 g of $Nd(CH_3COO)_3.xH_2O$ and 65 g of $H_2O$ are added (solution A). A second solution (solution B) is prepared containing 20 g of water, 1.6 g of LiOH and 2.25 g of TPAOH (tetrapropyl ammonium hydroxide) (53% by weight).

Solution B is added to solution A under vigorous stirring at ambient temperature (about 25° C.) and the mixture homogenized for 15 minutes. The atomic Li:Mg:Nd ratio in the resultant solution is 40:40:20. The partly gelled solution is left standing for 18 hours. The product obtained in this manner is dried at 110° C. for 5 hours to obtain a metal oxide mixture (5.0 wt % lithium content) which is then heated for 4 hours to 800° C. in an air stream. It is finally cooled to recover a solid with a lithium content of 3.3% by weight.

EXAMPLE 2

4.3 g of $Mg(CH_3COO)_2.4H_2O$ are dissolved in a beaker containing 15 g of $H_2O$ acidified with 0.5 ml of $HNO_3$ (65% by weight). After acidifying with a further 1.5 ml of $HNO_3$ (65% by weight), 10.9 g of $Nd(CH_3COO)_3.xH_2O$ and 65 g of $H_2O$ are added (solution A). A second solution (solution B) is prepared containing 30 g of water, 3.2 g of LiOH and 2.25 g of TPAOH (53% by weight). Solution B is added to solution A under vigorous stirring at ambient temperature (about 25° C.) and the mixture homogenized for 15 minutes. The atomic Li:Mg:Nd ratio in the resultant solution is 57:29:14. The partly gelled solution is left standing for 18 hours. The product obtained in this manner is dried at 110° C. for 5 hours to obtain a metal oxide mixture (9.0 wt % lithium content) which is then heated for 5 hours to 800° C. in an air stream. It is finally cooled to recover a solid with a lithium content of 3.9% by weight.

EXAMPLE 3

14.3 g of $Mg(CH_3COO)_2.4H_2O$ are dissolved in a beaker containing 15 g of $H_2O$ acidified with 0.5 ml of $HNO_3$ (65% by weight). After acidifying with a further 1.5 ml of $HNO_3$ (65% by weight), 10.9 g of $Nd(CH_3COO)_3.xH_2O$ and 65 g of $H_2O$ are added (solution A). A second solution (solution B) is prepared containing 10 g of water, 0.4 g of LiOH and 2.25 g of TPAOH (53% by weight). Solution B is added to solution A under vigorous stirring at ambient temperature (about 25° C.) and the mixture homogenized for 15 minutes. The atomic Li:Mg:Nd ratio in the resultant solution is 14:57:29. The partly gelled solution is left standing for 18 hours. The product obtained in this manner is dried at 110° C. for 5 hours to obtain a metal oxide mixture (1.3 wt % lithium content) which is then heated for 4 hours to 800° C. in an air stream. It is finally cooled to recover a solid with a lithium content of 1.0% by weight.

EXAMPLE 4 (Comparison)

14.3 g of $Mg(CH_3COO)_2.4H_2O$ are dissolved in a beaker containing 15 g of $H_2O$ acidified with 0.5 ml of $HNO_3$ (65% by weight). After acidifying with a further 1.5 ml of $HNO_3$ (65% by weight), 10.9 g of $Nd(CH_3COO)_3.xH_2O$ and 65 g of $H_2O$ are added (solution A). A second solution (solution B) is prepared containing 10 g of water, 0.08 g of LiOH and 2.25 g of TPAOH (53% by weight). Solution B is added to solution A under vigorous stirring at ambient temperature (about 25° C.) and the mixture homogenized for 15 minutes. The atomic Li:Mg:Nd ratio in the resultant solution is 3:65:32. The partly gelled solution is left standing for 18 hours. The product obtained in this manner is dried at 110° C. for 5 hours to obtain a metal oxide mixture (0.28 wt % lithium content) which is then heated for 4 hours to 800° C. in an air stream. It is finally cooled to recover a solid with a lithium content of 0.16% by weight.

EXAMPLE 5 (Comparison)

14.3 g of $Mg(CH_3COO)_2.4H_2O$ are dissolved in a beaker containing 15 g of $H_2O$ acidified with 0.5 ml of $HNO_3$ (65% by weight). After acidifying with a further 1.5 ml of $HNO_3$ (65% by weight), 10.9 g of $Nd(CH_3COO)_3.xH_2O$ and 65 g of $H_2O$ are added (solution A). A second solution (solution B) is prepared containing 5 g of water, 0.020 g of LiOH and 2.25 g of TPAOH (53% by weight). Solution B is added to solution A under vigorous stirring at ambient temperature (about 25° C.) and the mixture homogenized for 15 minutes. The atomic Li:Mg:Nd ratio in the resultant solution is 0.8:66.1:33.1. The partly gelled solution is left standing for 18 hours. The product obtained in this manner is dried at 110° C. for 5 hours to obtain a metal oxide mixture (0.07 wt % lithium content) which is then heated for 4 hours to 800° C. in an air stream. It is finally cooled to recover a solid with a lithium content of 0.05% by weight.

EXAMPLE 6

14.3 g of $Mg(CH_3COO)_2.4H_2O$ are dissolved in a beaker containing 15 g of $H_2O$ acidified with 0.5 ml of $HNO_3$ (65% by weight). After acidifying with a further 1.5 ml of $HNO_3$ (65% by weight), 10.9 g of $Nd(CH_3COO)_3.xH_2O$ and 65 g of $H_2O$ are added. Under continuous stirring, the perfectly clear solution is heated to 120° C. in a nitrogen stream to substantially completely evaporate the excess aqueous solvent. The product is dried in an oven at 150° C. for 2 hours, the solid obtained then being calcined in a muffle furnace at 550° C. for 4 hours in an air stream. Under stirring, 20 ml of an aqueous solution containing 1.6 g of lithium hydroxide are slowly added to this product. It is dried in an oven at 150° C. for 2 hours to obtain a dry solid with an atomic Li:Mg:Nd ratio of 40:40:20 (5.0 wt % lithium content), which is heated for 4 hours to 800° C. in an air stream. It is finally cooled to recover a solid with a lithium content of 2.5% by weight,

EXAMPLE 7 (Comparison)

14.3 g of $Mg(CH_3COO)_2.4H_2O$ are dissolved in a beaker containing 15 g of $H_2O$ acidified with 0.5 ml of $HNO_3$ (65% by weight). After acidifying with a further 1.5 ml of $HNO_3$ (65% by weight), 10.9 of g $Nd(CH_3COO)_3.xH_2O$ and 65 g of $H_2O$ are added. Under continuous stirring, the perfectly clear solution is heated to 120° C. in a nitrogen stream to substantially completely evaporate the excess aqueous solvent. The product is dried in an oven at 150° C. for 2 hours, the solid obtained then being calcined in a muffle furnace at 550° C. for 4 hours in an air stream. Under stirring, 20 ml of an aqueous solution containing 0.020 g of lithium hydroxide are slowly added to this product. The resultant mixture is dried in an oven at 150° C. for 2 hours to obtain a dry solid with an atomic Li:Mg:Nd ratio of 0.8:66.1:33.1 (0.07 wt % lithium content), which is heated for 4 hours to 800° C. in an air stream. It is finally cooled to recover a solid with a lithium content of 0.04% by weight.

EXAMPLE 8

14.3 g of $Mg(CH_3COO)_2.4H_2O$ are dissolved in a beaker containing 15 g of $H_2O$ acidified with 0.5 ml of $HNO_3$ (65% by weight). After acidifying with a further 1.5 ml of $HNO_3$ (65% by weight), 13.9 g of $La(CH_3COO)_3.xH_2O$ and 65 g of $H_2O$ are added (solution A). A second solution (solution B) is prepared containing 20 g of water, 1.6 g of LiOH and 2.25 g of TPAOH (53% by weight). Solution B is added to solution A under vigorous stirring at ambient temperature (about 25° C.) and the mixture homogenized for 15 minutes. The atomic Li:Mg:La ratio in the resultant solution is 40:40:20. The partly gelled solution is left standing for 18 hours. The product obtained in this manner is dried at 110° C. for 5 hours to obtain a metal oxide mixture (5.0 wt % lithium content) which is then heated for 4 hours to 800° C. in an air stream. It is finally cooled to recover a solid with a lithium content of 3.1% by weight.

EXAMPLE 9 (Comparison)

4.3 g of $Mg(CH_3COO)_2.4H_2O$ are dissolved in a beaker containing 15 g of $H_2O$ acidified with 0.5 ml of $HNO_3$ (65% by weight). After acidifying with a further 1.5 ml of $HNO_3$ (65% by weight), 10.9 g of $Nd(CH_3COO)_3.xH_2O$ and 65 g of $H_2O$ are added. Under continuous stirring, the perfectly clear solution is heated to 120° C. in a nitrogen stream to substantially completely evaporate the excess aqueous solvent. The product is dried in an oven at 150° C. for 2 hours, the solid obtained then being calcined in a muffle furnace at 800° C. for 4 hours in an air stream. In the resultant solid the atomic Li:Mg:Nd ratio is 0:67:33.

EXAMPLE 10

1.5 g of each of the catalyst precursors obtained in Examples 1 to 9 are placed in a fixed-bed tubular quartz microreactor with an internal diameter of 10 mm. Helium-diluted methane and oxygen with a molar methane/oxygen ratio of 4.0 and a methane partial pressure of 0.47 are fed to the reactor. The catalyst precursors are maintained at a temperature of 770° C. for 18 hours, after this treatment the lithium content generally being of the order of 0.10% by weight (except for Example 9). The methane conversion test is conducted after this treatment operating at atmospheric pressure and a temperature of 920° C. measured by a thermocouple immersed in the catalyst, and with a contact time of 0.0018 min/g cat/ml gas (the gas feed volume being evaluated under normal conditions). Each test lasts 60 hours.

The results shown in Table 1 were obtained after 50 hours of reaction, when the catalyst performance was stable.

TABLE 1

| Ex. | $CH_4$ conversion | Selectivity | | | | | Yield |
|---|---|---|---|---|---|---|---|
| | | CO | $CO_2$ | $C_2H_4$ | $C_2H_6$ | $C_{2+}$ | $C_{2+}$ |
| 1 | 28.1 | 13.2 | 23.4 | 32.4 | 27.4 | 63.4 | 17.8 |
| 2 | 27.1 | 14.3 | 22.7 | 29.8 | 29.7 | 63.0 | 17.1 |
| 3 | 26.9 | 14.4 | 26.8 | 26.4 | 28.9 | 58.8 | 15.8 |
| 4 | 25.8 | 13.8 | 29.8 | 25.6 | 27.8 | 56.4 | 14.6 |
| 5 | 23.6 | 13.1 | 37.2 | 21.5 | 25.8 | 49.7 | 11.7 |
| 6 | 26.9 | 13.2 | 24.7 | 29.2 | 29.0 | 62.1 | 16.7 |
| 7 | 22.4 | 12.7 | 42.1 | 18.6 | 23.7 | 45.2 | 10.3 |
| 8 | 27.0 | 13.0 | 28.0 | 28.9 | 25.9 | 59.0 | 16.0 |
| 9 | 23.6 | 12.2 | 39.4 | 19.5 | 25.4 | 48.4 | 11.4 |

In the aforegoing table the $CH_4$ conversion signifies the percentage of feed methane converted. In addition, the selectivity (in % C) and the yield (in % C) refer to the converted reagent and to the feed reagent respectively. Finally, $C_{2+}$, signifies paraffinic or olefinic products with 2 or more carbon atoms.

The lithium content of each catalyst was determined at the end of each test, this being always of the order of 0.10% by weight (except for example 9). There were no variations in the other elements from the starting compositions.

EXAMPLE 11

A long-duration test was conducted to determine the variation in the activity and selectivity of the catalyst of Example 1 with time.

For this purpose, 1.5 g are placed in the microreactor of Example 10 and treated as described in said example. The test is conducted for 900 hours, feeding helium-diluted methane and oxygen with a molar methane/oxygen ratio of 3.0 and a methane partial pressure of 0.19. The operating pressure is atmospheric, with a temperature of 900° C. measured by a thermocouple immersed in the catalyst, and a contact time of 0.0018 min/g cat/ml gas.

BRIEF DESCRIPTION OF THE DRAWING

The FIGURE shows the variation in the percentage activity [vertical axis, curve (. . .)] and percentage selectivity [vertical axis, (curve (+ + +)] with time in hours, represented by the horizontal axis resulting in the data accumulated in Example 11.

What is claimed is:

1. A process for converting methane (by oxidative coupling) into higher hydrocarbon products, said process being characterized in contacting a gaseous mixture containing methane and oxygen, at a temperature of at least 650° C., with a solid catalyst formed from lithium oxide, an alkaline earth metal oxide and a lanthanide oxide, in which the lithium content is less than 20% by weight and the atomic ratio of the alkaline earth metal to the lanthanide varies from 0.8/1 to 8/1, said catalyst being obtained by:

preparing a mixture of lithium, alkaline earth metal and lanthanide oxides in which the lithium content exceeds 1% by weight; and reducing the lithium content in the mixture by heating the mixture at least partly in an oxidizing atmosphere for a time sufficient to reduce the lithium content to less than 0.20% by weight.

2. A process as claimed in claim 1, characterised in that the lithium content of the initial oxide mixture varies from 4 to 10% by weight, the lithium content being reduced to a value of about 0.1% by weight in the final catalyst.

3. A process as claimed in claim 1, characterised in that the lithium content is reduced by heating the oxide mixture in an oxygen stream or a gas stream containing oxygen, to a temperature between about 700° and 900° C. for a time of between 3 and 30 hours.

4. A process as claimed in claim 1, characterised in that the atomic ratio of the alkaline earth metal to the lanthanide in the oxide mixture and in the final catalyst varies from 2/1 to 4/1.

5. A process as claimed in claim 1, characterised in that the alkaline earth metal is magnesium and the lanthanide is neodymium or lanthanum.

6. A process as claimed in claim 1, characterised in that the methane oxidative coupling reaction is effected by operating with the catalyst in the form of a fixed bed to which a gaseous stream is fed containing methane and oxygen with a methane/oxygen molar ratio of between 1.5/1 and 10/1, operating at a temperature of between 650° and 1000° C. for a contact time of about 0.0005–0.02 minutes per gram of catalyst per millilitre of gas feed.

7. A process as claimed in claim 3, wherein the gas stream containing oxygen is air.

8. A process as claimed in claim 1, wherein the lithium content is partially eliminated under the oxidizing atmosphere and thereafter further eliminated in the presence of methane and oxygen, wherein the coupling reaction is effected by operating at a temperature on the order of 700°–800° C.

9. A process as claimed in claim 6, wherein the gaseous stream further contains an inert gas.

10. A process as claimed in claim 6, wherein the methane/oxygen molar ratio is between 1.8/1 and 5/1.

11. A process as claimed in claim 10, wherein the coupling reaction is effected by operating at a temperature of between 800° C. and 950° C.

* * * * *

UNITED STATES PATENT AND TRADEMARK OFFICE
CERTIFICATE OF CORRECTION

PATENT NO. : 5,321,188
DATED : June 14, 1994
INVENTOR(S) : Giuseppe Fornassari, Stefano Palmery, Giampiero Piro and Giuseppe Bellussi It is certified that error appears in the above-indentified patent and that said Letters Patent is hereby corrected as shown below:

Column 6, line 65,
In Claim 1, line 7, delete "20%" and insert --0.20%--.

Signed and Sealed this

Twenty-seventh Day of August, 1996

Attest:

BRUCE LEHMAN

Attesting Officer

Commissioner of Patents and Trademarks